United States Patent [19]
Wu

[11] Patent Number: 5,475,170
[45] Date of Patent: Dec. 12, 1995

[54] HALOALKYLATION PROCESS

[75] Inventor: Tse-Chong Wu, Baton Rouge, La.

[73] Assignee: Albermarle Corporation, Richmond, Va.

[21] Appl. No.: 266,398

[22] Filed: Jun. 27, 1994

[51] Int. Cl.⁶ .......................... C07C 17/10; C07C 17/00
[52] U.S. Cl. .................................................. 570/191
[58] Field of Search ................................. 570/190, 191, 570/192

[56] References Cited

U.S. PATENT DOCUMENTS

| | | | |
|---|---|---|---|
| 4,536,595 | 8/1985 | Gardano et al. | 562/406 |
| 5,099,083 | 3/1992 | Thomas et al. | 570/194 |

FOREIGN PATENT DOCUMENTS 3930993  3/1991  Germany.

Primary Examiner—Werren B. Lone
Attorney, Agent, or Firm—Philip M. Pippenger

[57] ABSTRACT

An improvement in a process for the haloalkylation of a first aromatic compound having at least one free ring position with a haloalkylating reagent and in the presence of a haloalkylation catalyst, said process producing a haloalkylated first aromatic compound and a dimeric reaction by-product of said first aromatic compound having at least one free ring position, the improvement comprising treating said by-product with a second aromatic compound having at least one free ring position the same or different than said first aromatic compound in the presence of a catalytically effective amount of an acid for a time and at a temperature sufficient to cleave said diarylalkane by-product and produce thereby said first aromatic compound having at least one free ring position.

10 Claims, No Drawings

HALOALKYLATION PROCESS

FIELD OF INVENTION

This invention relates to an improvement in the haloalkylation process as applied to aromatic compounds.

BACKGROUND OF THE INVENTION

Friedel-Crafts reactions are well known and have been summarized in monographs such as Olah, G. A. et al., *Friedel-Crafts Chemistry*, John Wiley & Sons, 1973, as well as other comprehensive reviews. See for example Thomas, C. A., *Anhydrous Aluminum Chloride in Organic Chemistry*, Reinhaldt Publishing Corp., New York, 1961.

Generally, such reactions are considered as any substitution, isomerization, elimination, cracking polymerization, or addition reaction that takes place under the catalytic effect of Lewis acid-type acidic halides (with or without co-catalysts) or proton acids.

In a specific case of a Friedel Crafts-type reaction it is known that aromatic compounds can be haloalkylated by reacting them with a hydrogen halide and an appropriate aldehyde, or with an α-haloalkyl ether or an α-haloalkyl alkyl ether, in the presence of a Lewis acid or a proton acid as a catalyst, most commonly, in the presence of zinc chloride.

The haloalkylations utilizing formaldehyde or a formaldehyde-derived ether have been successfully employed in providing fairly high yields of 1-halo-1-arylalkanes. Reasonably high yields of 1-halo-1-arylalkanes have sometimes also been obtained from haloalkylations utilizing higher aldehydes or ethers derived from them. However, it has frequently not been found possible to provide commercially acceptable yields of 1-halo-1-arylalkane from the higher aldehydes and ethers, especially when the aromatic compound has been one of the less reactive ones, such as a monoalkylaromatic hydrocarbon. There has been too much co-formation of diaryl-alkane by-product.

SUMMARY OF THE INVENTION

It has now been discovered that the by-product dimer formed from the Friedel Crafts haloalkylation reaction can be catalytically treated with a second aromatic compound either the same or different than the first aromatic compound used in the haloalkylation reaction to cleave the dimer and regenerate the first aromatic compound.

DESCRIPTION OF THE PREFERRED EMBODIMENTS

As noted, the haloalkylation process produces an undesirable amount of dimeric by-product.

It has now been discovered that this dimeric product may be readily cleaved by treating it with a second aromatic compound (an aromatic compound having at least one free ring position) that may be the same or different than the first aromatic compound.

The treatment is carried out in the presence of an effective amount of a catalyst that may be one or more of the Friedel Crafts catalysts described herein or it may be a proton acid, and acid resin, acid zeolite, clays, silicas, and the like.

Thus, in the chloroethylation of isobutylbenzene to form 1-chloro-1-phenylethane, large amounts of 1,1-bis(p-isobutylphenyl)ethane are formed. Treatment of this dimeric by-product with benzene, toluene, etc. or other alkylated benzenes under acidic conditions preferably with a Lewis acid or proton and as described herein, regenerate the starting materials of the haloalkylation reaction (isobutylbenzene). The alkylated benzene forms the dimeric compound, e.g., benzene forms 1,1-diphenylethane.

The first aromatic compound employed in the practice of this invention are those having at least one free ring proton and may be a carbocyclic aromatic compound, e.g., an unsubstituted aromatic hydrocarbon, such as benzene, naphthalene, anthracene, phenanthrene, etc.; a polyalkylaromatic hydrocarbon, such as xylene, pseudocumene, mesitylene, etc.; an aromatic hydrocarbon bearing a substituent such as halo, cyano, nitro, hydroxy, alkoxy, phenoxy, alkylthio, etc. (e.g., the 2-, 3-, and 4-chloronitrobenzenes, the 2-, 3-, and 4-fluoronitrobenzenes, 4-fluoronitrobiphenyl, 6-methoxynapthalene, phenoxybenzene, etc.); or it may be a heterocyclic aromatic compound, such as chlorocarbazole, 2-phenyl-1-isoindolinone, 6-fluoro-5-nitro-quinoline, etc. However, because of the commercial interest in their haloalkylated products and the difficulty that has previously been encountered in preparing the desired 1-halo-1-arylalkanes from them, the preferred aromatic compounds are monoalkylaromatic hydrocarbons, such as 1-methylnaphthalene, 2-methoxynaphthalene, 9-methylanthracene, 9-butylanthracene, 9-dodecylanthracene, and the various monoalkylbenzenes, e.g., the methyl-, ethyl-, propyl-, isobutyl-, secbutyl-, t-butyl-, isopentyl-, t-pentyl-, and hexylbenzenes. The most preferred aromatic compounds are the monoalkylbenzenes wherein the alkyl group contains 1–5 carbons.

The most frequently used haloalkylating agents are: aldehydes with hydrogen halides, haloalkyl ethers, haloalkyl sulfides, acetals with hydrogen halides, di- and polyhaloalkanes, haloalkenes, haloalcohols, haloalkyl sulfates, haloalkyl p-tosylates, and miscellaneous haloalkyl inorganic acid esters.

The preferred haloalkylating agents of use in practicing the improved process herein are aldehydes and hydrogen halides as well as haloalkyl ethers.

In one embodiment of the present invention, the haloalkylation reaction is carried out with an ether. The ether which is reacted with the aromatic hydrocarbon is an ether corresponding to the formula R—O—R', wherein R is an α-chloroalkyl group containing at least two carbons, preferably 2–20 carbons, and most preferably 2–6 carbons, and R' is R or an alkyl group which preferably contains 1–20 carbons most preferably 1–6 carbons.

Exemplary of the ethers which may be employed are α-chloroethyl ether [also known as chloroethyl ether, 1-chloro-ethyl ether, bis(1-chloroethyl)ether, or di(1-chloroethyl)ether], α-chloropropyl ether, α-chlorobutyl ether, α-chloropentyl ether, α-chlorododecyl ether, α-chloropentadecyl ether, α-chloro-octadecyl ether, α-chloroeicosyl ether, α-chloroethyl methyl ether, α-chloroethyl ethyl ether, α-chloroethyl propyl ether, α-chlorobutyl butyl ether, α-chloropentyl methyl ether, α-chloro-hexyl ether, etc. The preferred ethers are the α-chloro-alkyl ethers, such as α-chloroethyl ether.

When not already available, the ethers may be formed by the conventional technique of reacting hydrogen chloride with the appropriate aldehyde and, when a chloroalkyl alkyl ether is desired, also with the appropriate alcohol to form the desired ether and water. The water may or may not be removed from the reaction product before the ether is used in the haloalkylation process, but it is generally preferred to remove any water that would cause the water content of the haloalkylation reaction mixture to exceed about 15% by weight of the catalyst used.

The amount of ether employed in the haloalkylation reaction may be as small as the stoichiometric amounts, i.e., the amount which provides one R group per molecule of aromatic hydrocarbon. However, it is generally preferred to employ an amount that provides at least two R groups per molecule of aromatic compound.

The above embodiment is useful as an alternative method of preparing 1-halo-1-arylalkanes from aromatic compounds that are known to be capable of providing high yields of such products by known haloalkylation techniques. However, it is particularly advantageous as a method of preparation 1-halo-1-arylalkanes from the less reactive aromatic hydrocarbons, such as monoalkyl-benzenes, that have not previously been found to be capable of providing high yields of such products by haloalkylation processes other than halomethylations.

As noted herein, the catalysts of use in the Friedel Crafts process are catalytically effective amounts of the Lewis acid-type and include the proton acids such as HF and $H_2SO_4$ as well as halides of zinc, aluminum, gallium, iron (III), antimony, zirconium, tin and boron. A particularly preferred catalyst used in carrying out Friedel Crafts-type of reactions is aluminum chloride. The reaction is conducted for a time and at a temperature necessary to generate the product, typically temperatures from about 25°–100° C. for from about 15 minutes to about 24 hours.

In another embodiment of the present invention, the haloalkylation reaction is carried out with an aldehyde and a hydrogen halide.

The aldehyde which is reacted with the aromatic hydrocarbon has the formula R"CHO wherein R" is hydrogen or an alkyl group which preferably contains 1 to 20 carbons atoms, most preferably 2 to 6 carbon atoms.

Exemplary of the aldehydes which may be employed are acetaldehyde, propionaldehyde, n-butyraldehyde, isobutyraldehyde, n-valeraldehyde, isovaleraldehyde, n-caproaldehyde, hepta-aldehyde, steraldehyde, and the like. Most preferably, the aldehyde is acetaldehyde.

The haloalkylation reaction with the above aldehydes require a hydrogen halide, the halide substituting as the alkyl group being added onto the aromatic ring. Thus, for an chloro-alkylation, the hydrogen halide must be hydrogen chloride; for a bromoalkylation, it must be hydrogen bromide.

The catalysts set forth for the haloalkylation reaction of aromatic hydrocarbons with ethers are also of use in this embodiment of the present invention.

As is known, the products obtained by the process are useful as internal standards, intermediates for the preparation of monomers, detergents, pharmaceuticals, etc. When they are used as chemical intermediates, they may be subjected to the same reactions as have previously been used to convert them to desired products. For example, the 1-halo-1-phenylethanes can be dehydrohalogenated in any known manner to provide styrenes which can then be polymerized by known techniques.

A particularly interest application of the 1-halo- 1-(4-alkylphenyl)ethanes, which are prepared in a preferred embodiment of the invention is as intermediates for the preparation of ibuprofen and related pharmaceuticals. When they are used in such applications, they may be converted to the desired products in any suitable manner. For example, they may be reacted with carbon monoxide in the presence of a carbonylation catalyst and then acidified to the corresponding propionic acids as in Gardano et al., U.S. Pat. No. 4,536,595; Francalanci et al., Canadian Patent No. 1,197,254; or Dynamit Nobel, British Patent No. 1,560,082; or they may be cyanated and then acidified to the corresponding propionic acids as in Palecek et al., Czechoslovakian Certificate 219,752, or Tokutake, Japanese Kokai 52-111536. Another useful synthesis involves reacting the compounds with magnesium, carbonating the resultant Grignard reagent with carbon dioxide, and acidifying the carbonated product to the propionic acid as in Miyatake et al., Japanese Kokai 47-39050.

The following examples are presented for the purpose of illustration only and are not to be regarded as limiting the invention as set forth in the claims in any way.

EXAMPLE 1

DBPE [1,1-bis (p-isobutylphenyl)ethane] (5.00 g, 17.0 mmol), benzene (40.0 g), $(CF_3SO_2)_2O$ (2.82 g, 10.0 mmol), and $H_2O$ (0.2 Ml) were added to an autoclave (Hastelloy C, 100 Ml). The autoclave was set up in the hood and then purged with $N_2$ for 10 minutes. The mixture was heated at 125° C. for 14 h. Gas chromatograph (GC) analysis of an aliquot showed a complete conversion. The reaction mixture contained ethylbenzene (2.5 GC area %), isobutylbenzene (64.1%), p-ethylisobutylbenzene (2.9%), and 1,1-diphenylethane (24.8%).

EXAMPLE 2

A mixture of $AlCl_3$ (0.40 g, 3.0 mmol), DBPE 91.0 g, 3.4 mmol), and benzene (15 g) was refluxed under nitrogen for 4 h. Gas chromatograph (GO) analysis showed a complete conversion. The reaction mixture contained ethylbenzene (12.4 GC area %), isobutylbenzene (61.2%), and 1,1-diphenylethane (11.8%).

EXAMPLE 3

A mixture of $AlCl_3$ (0.40 g, 3.0 mmol), DBPE (1.0 g, 3.4 mmol), and toluene (15 g) was stirred under nitrogen at 105° C. for 4 h. Gas chromatograph (GC) analysis of an aliquot showed a complete conversion. The reaction mixture contained ethyltoluene (18.7 GC area %), isobutylbenzene (48.6%), isobutyltoluene (20.8%), and 1-(p-isobutylphenyl)- 1-tolylethane (9.6%).

EXAMPLE 4

Amberlyst 35 (1.0 g), DBPE (4.5 g), and benzene (30 g) were added to an autoclave (Hastelloy C, 100 Ml). The autoclave was set up in the hood and then purged with $N_2$ for 10 minutes. The mixture was heated at 150° C. for 30 h. GC analysis of an aliquot showed that the reaction mixture contained isobutylbenzene (3.4 GC area %), 1-(4-isobutylphenyl)- 1-phenylethane (4.0%) and unreacted DBPE (90%).

EXAMPLE 5

DBPE (2.0 g), benzene (30 g), and $H_2SO_4$ (95%, 3.0 g) were added to an autoclave (Hastelloy C, 100 Ml). The autoclave was set up in the hood and then purged with $N_2$ for 10 minutes. The mixture was heated at 130° C. for 7 h. GC analysis of an aliquot showed that the reaction mixture contained isobutylbenzene (28 GC area %), p-ethylisobutylbenzene (0.7%), 1,1-diphenylethane (3.1%), 1-(4-isobutylphenyl)-1-phenylethane (11%) and unreacted DBPE (58%).

I claim:

1. In a process for the haloalkylation of a first aromatic compound having at least one free ring position with a haloalkylating reagent and in the presence of a haloalkylation catalyst, said process producing a haloalkylated first aromatic compound and a dimeric reaction by-product of said first aromatic compound having at least one free ring position, the improvement comprising treating said by-product with a second aromatic compound having at least one free ring position the same or different than said first aromatic compound in the presence of a catalytically effective amount of an acid for a time and at a temperature sufficient to cleave said diarylalkane by-product and produce thereby said first aromatic compound having at least one free ring position.

2. The process according to claim 1 wherein said first aromatic compound having at least one free ring position is a monoalkylbenzene.

3. The process according to claim 2 wherein said monoalkylbenzene is one in which the alkyl group is 1 to 5 carbon atoms.

4. The process according to claim 3 wherein said monoalylbenzene is isobutylbenzene.

5. The process according to claim 1 wherein said haloalkylating reagent is a dialkylether having the formula R—O—R', wherein R is an α-chloroalkyl group containing at least two carbon atoms and R is an alkyl group.

6. The process according to claim 5 wherein R is an α-chloroalkyl group containing 2–6 carbon atoms and R' is R or an alkyl group having 1–6 carbon atoms.

7. The process according to claim 6 wherein said dialkylether is α-chloroethyl ether.

8. The process according to claim 1 wherein said second aromatic compound having at least one free ring position is a benzene or a monoalkylated benzene.

9. The process according to claim 8 wherein said second aromatic compound is benzene.

10. The process according to claim 1 wherein said acid is a Lewis acid.

* * * * *